United States Patent
Sugiura (10) Patent No.: US 7,406,871 B2
(45) Date of Patent: Aug. 5, 2008

(54) FUEL TYPE IDENTIFYING APPARATUS

(75) Inventor: Makiko Sugiura, Hekinan (JP)

(73) Assignee: DENSO CORPORATION, Kariay (JP)

( * ) Notice: Subject to any disclaimer, the term of this patent is extended or adjusted under 35 U.S.C. 154(b) by 452 days.

(21) Appl. No.: 11/032,222

(22) Filed: Jan. 11, 2005

(65) Prior Publication Data
US 2005/0172700 A1 Aug. 11, 2005

(30) Foreign Application Priority Data
Jan. 13, 2004 (JP) ............................. 2004-005461

(51) Int. Cl.
*G01N 29/00* (2006.01)
*F02B 33/00* (2006.01)

(52) U.S. Cl. ............................ 73/592; 73/299; 73/301; 123/25 C; 123/198 D (58) Field of Classification Search ................... 73/299, 73/290 R, 291, 292, 301, 302, 592; 340/614; 123/25 C, 198 D
See application file for complete search history.

(56) References Cited

U.S. PATENT DOCUMENTS

| 3,910,216 | A | * | 10/1975 | Shultz .......................... 114/275 |
| 4,355,363 | A | * | 10/1982 | Colby et al. ................... 702/52 |
| 4,590,797 | A | * | 5/1986 | Beaubatie et al. ............. 73/295 |
| 5,644,069 | A | | 7/1997 | Liu et al. |
| 5,701,863 | A | * | 12/1997 | Cemenska et al. ....... 123/198 D |
| 5,775,164 | A | * | 7/1998 | Kishi ........................ 73/304 R |
| 6,539,796 | B2 | * | 4/2003 | Shirai et al. .................... 73/299 |
| 6,597,998 | B1 | * | 7/2003 | Gonring ....................... 702/55 |
| 6,931,926 | B1 | * | 8/2005 | Van Ee .......................... 73/299 |
| 7,051,573 | B2 | * | 5/2006 | Bresciani et al. ........... 73/23.34 |
| 7,152,582 | B2 | * | 12/2006 | Takahata et al. ....... 123/406.12 |

FOREIGN PATENT DOCUMENTS

| JP | A-UM-H02-012037 | 1/1990 |
| JP | A-H02-181064 | 7/1990 |
| JP | A-H03-133795 | 6/1991 |

(Continued)

OTHER PUBLICATIONS

Notification of Reasons for Refusal dated Nov. 12, 2007 in corresponding Japanese Patent Application No. 2004-005461 (and English translation).

(Continued)

*Primary Examiner*—Hezron E. Williams
*Assistant Examiner*—Jacques M. Saint-Surin
(74) *Attorney, Agent, or Firm*—Posz Law Group, PLC (57) ABSTRACT

A fuel tank is allowed to hold any of types of liquid fuels and currently hold one type of liquid fuel. A light emitting element outputs a light beam of a predetermined emission spectrum to the liquid fuel of the fuel tank. The liquid fuel changes the light beam to a reflected light beam of a reflection spectrum according to spectral characteristics of the liquid fuel. The reflection spectrum is peculiar to the type of the liquid fuel of the fuel tank. A light receiving element detects the reflection spectrum, and a control circuit receives the detected reflection spectrum from the light receiving element. The control circuit collates the detected reflection spectrum with a referential reflection spectrum corresponding to each fuel type and identified the type of the liquid fuel of the fuel tank according to a collation result.

12 Claims, 3 Drawing Sheets

FOREIGN PATENT DOCUMENTS

| | | |
|---|---|---|
| JP | A-H05-223026 | 8/1993 |
| JP | A-H05-249037 | 9/1993 |
| JP | A-H07-260773 | 10/1995 |
| JP | A-H09-005303 | 1/1997 |
| JP | 9-158731 | 6/1997 |
| JP | A-H10-176557 | 6/1998 |
| JP | A-H11-013568 | 1/1999 |
| JP | A-2003-314316 | 11/2003 |

OTHER PUBLICATIONS

Office Action dated Feb. 19, 2008 in corresponding Japanese Patent Application No. 2004-005461 (and English translation).

* cited by examiner

FUEL TYPE IDENTIFYING APPARATUS

CROSS-REFERENCE TO RELATED APPLICATION

This application is based upon and claims the benefit of priority of the prior Japanese Patent Application 2004-005461 filed on Jan. 13, 2004 so that the contents of which are incorporated herein by reference.

BACKGROUND OF THE INVENTION

1. Field of the Invention

The present invention relates to a fuel type identifying apparatus which identifies a type of a liquid fuel held in a fuel tank.

2. Description of Related Art

The structure of a conventional internal combustion engine and a combustion method in the engine depend on a type of a liquid fuel used in the engine. For example, in case of a gasoline engine, gasoline is used as a fuel, and the gasoline is mixed with air at the optimum ratio to obtain an air-fuel mixture. The air-fuel mixture is fed into a cylinder of the engine and is compressed in the cylinder. The compressed air-fuel mixture is ignited by using a spark plug, thereby being exploded. Further, in case of a diesel engine, light oil is used as a fuel, only air is initially fed and compressed into/in a cylinder of the engine, and then light oil is injected into the cylinder to explode a mixture of the air and light oil due to a self ignition. As another combustion method for the gasoline engine, similarly to the self ignition in the diesel engine, a technique of the self ignition applied to the gasoline engine has been researched to reduce a fuel consumption of the gasoline engine.

Further, a diesel engine using kerosene or vegetable oil as a fuel has been proposed. For example, Published Japanese Patent First Publication No. H09-158731 discloses this diesel engine. Particularly, because vegetable oil can be mass-produced due to biotechnology, a diesel engine using the vegetable oil is called a bio-diesel engine. In this bio-diesel engine, an exhaust gas can be reduced. Further, in consideration of exhaustion of the petroleum in the future, the spread of the bio-diesel engine has been expected.

Moreover, a multi-fuel engine operable by using any of a plurality of types of fuels has been proposed. In this engine, structural parts common to those of the conventional engine usable for only one type of fuel are used, so that the multi-fuel engine can be produced at low cost. Further, a user of this engine can freely select the fuel type, so that the user can reduce a cost of the fuel used for the engine.

However, in case of the engine operable by using any of the types of liquid fuels such as gasoline, diesel, vegetable oil and the like, operational conditions (for example, quantity of injected fuel, compression ratio in air-fuel mixture or air, valve timing and the like) optimum to the engine depend on the type of the fuel actually used for the engine. Therefore, it is required to change the operational conditions optimum to the engine for each fuel type so as to obtain fuel combustion conditions optimum to the type of the fuel actually used in the engine. Therefore, a fuel type identifying apparatus has been required to identify a type of a liquid fuel supplied to an engine.

SUMMARY OF THE INVENTION

An object of the present invention is to provide a fuel type identifying apparatus in which a type of a liquid fuel to be supplied to an engine is reliably distinguished.

According to a first aspect of this invention, the object is achieved by the provision of a fuel type identifying apparatus comprising a quantity detector and an identifying unit. The quantity detector detects a physical or chemical quantity from a liquid fuel held in a fuel tank and outputs a detection signal indicating the physical or chemical quantity. The physical or chemical quantity depends on a physical or chemical property of the liquid fuel. The identifying unit receives the detection signal from the quantity detector and identifies a type of the liquid fuel according to the physical or chemical quantity of the detection signal.

In this configuration, the physical or chemical quantity depends on a degree of the physical or chemical property of the liquid fuel, so that the physical or chemical quantity is peculiar to the physical or chemical quantity. Accordingly, the identifying unit can reliably identify a type of the liquid fuel according to the physical or chemical quantity obtained from the fuel.

DETAILED DESCRIPTION OF THE PREFERRED EMBODIMENTS

Embodiments of the present invention will now be described with reference to the accompanying drawings, in which like reference numerals indicate like parts, members or elements throughout the specification unless otherwise indicated.

Embodiment 1

The inventor of this application has noticed that a level of spectral characteristics of each of various types of liquid fuels differs from those of the other types in a predetermined range of wavelength, and a reflection (or reflectance) spectrum of light depends on the spectral characteristics when an emission spectrum of the light is fixed. The spectral characteristics represent a physical property, and the reflection spectrum represents a physical quantity depending on the physical or chemical property.

Figure 1A:
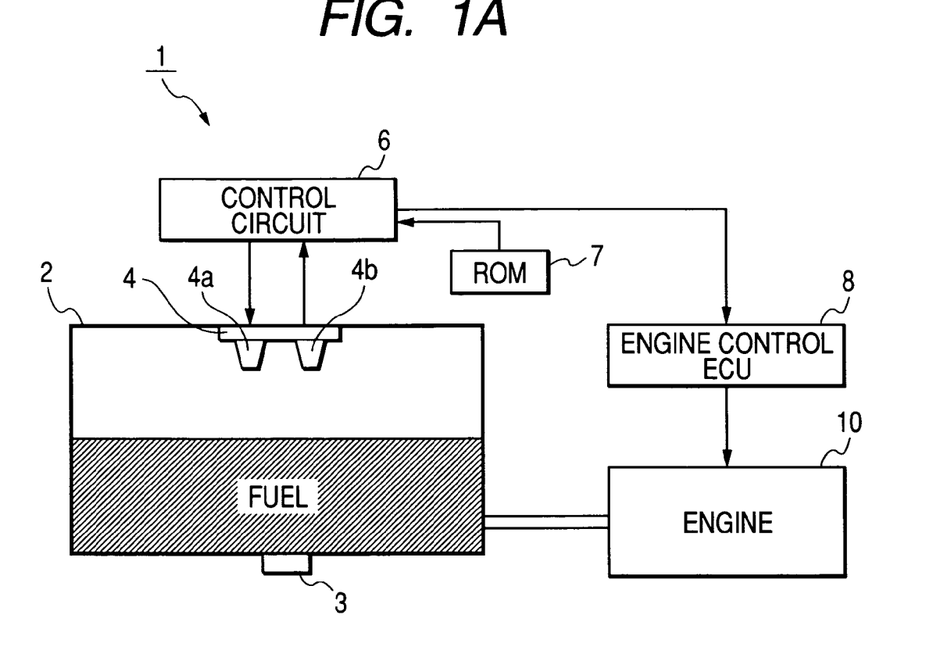
FIG. 1A is a view explanatorily and schematically showing a fuel type identifying apparatus according to a first embodiment of the present invention.

FIG. 1A is a view explanatorily and schematically showing a fuel type identifying apparatus according to a first embodiment.

As shown in FIG. 1A, a fuel tank 2 is mounted on a vehicle. a fuel type identifying apparatus 1 has a light sensor 4 attached on an inner upper surface (or a lid) of the fuel tank 2 and represents a quantity detector, a control circuit 6 representing an identifying unit, and a read only memory (ROM) 7 representing a data storage.

The fuel tank 2 is allowed to hold any of a plurality of types of liquid fuels such as gasoline, light oil, kerosene, vegetable oil, methyl tertiary butyl ether (MTBE), and the like, and currently holds one type of liquid fuel.

The light sensor 4 has a light emitting element 4a and a light receiving element 4b facing the upper surface of the liquid fuel. The light emitting element 4a representing a signal transmitter outputs a light beam of a predetermined emission spectrum as an investigation signal indicating. The light beam is, for example, an infrared radiation or a visible radiation. The spectrum of the light beam is changeable in response to spectral characteristics of each fuel type for light. The light emitting element 4a is, for example, made of a light emitting diode, a lamp, a semiconductor laser (or a laser diode), an electro luminescence device or the like. The light receiving element 4b representing a signal receiver receives a light beam reflected on the upper surface of the liquid fuel and outputs a detection signal indicating the reflected light beam. The reflected light beam has a reflection spectrum. The light receiving element 4b is, for example, made of a photo diode, a photo transistor, cadmium sulfide (CdS) device or the like.

The ROM 7 stores a referential reflection spectrum for each of the liquid fuels of the types allowed in the fuel tank 2. The referential reflection spectrum corresponding to each type of liquid is obtained in advance by putting the liquid fuel in a tank having the same depth as that of the fuel tank 2, emitting a light beam having the predetermined emission spectrum to the liquid fuel, receiving a light beam reflected on the surface of the liquid fuel, detecting a reflection spectrum of the reflected light beam, and storing the reflection spectrum in the ROM 7 as the referential reflection spectrum.

The control circuit 6 identifies the type of the fuel type currently of the fuel tank 2 according to the reflection spectrum detected by the light sensor 4 and the referential reflection spectra of the ROM 7.

In operation of the fuel type identifying apparatus 1, when an ignition switch (not shown) of a vehicle is turned on by a user of a vehicle, an operation start signal is transmitted to the control unit 6. The control unit 6 produces a driving signal in response to the operation start signal and outputs the driving signal to the light emitting element 4a. In response to the driving signal, the light emitting element 4a outputs a light beam having a predetermined emission spectrum toward the liquid fuel of the fuel tank 2. A portion of the emitted light beam is absorbed by the liquid fuel, and the other portion of the emitted light beam is reflected on the upper surface of the liquid fuel as a reflected light beam. The reflected light beam is returned to the light receiving element 4b, and the light receiving element 4b detects a reflection spectrum of the reflected light beam and outputs a detection signal indicating the reflection spectrum to the control circuit 6.

The predetermined emission spectrum of the emitted light beam is changed to the reflection spectrum of the reflected light beam according to the spectral characteristics of the liquid fuel, and spectral characteristics of each type of liquid fuel differ from those of the other fuel types. Therefore, the reflection spectrum of the light beam reflected on a liquid fuel is peculiar to the type of the liquid fuel.

The control circuit 6 receiving the detection signal retrieves a referential reflection spectrum corresponding to each fuel type from the ROM 7, and collates the detected reflection spectrum with the referential reflection spectrum for each type of liquid fuel. Thereafter, the control circuit 6 finds out a particular type of the liquid fuel corresponding to one referential reflection spectrum, which is the substantially same as the detected reflection spectrum, from the types of the liquid fuels. Therefore, the control circuit 6 distinguishes the liquid fuel currently of the fuel tank 2 as the particular fuel type.

Thereafter, the control circuit 6 outputs a fuel type signal indicating the particular fuel type to an electronic control unit (ECU) 8 for engine control. The engine control ECU 8 specifies properties (for example, octane number, cetane number, ignition temperature, viscosity and the like) of the liquid fuel of the type indicated by the fuel type signal of the control unit 6. Thereafter, the engine control ECU 8 determines operational conditions (for example, quantity of injected fuel, compression ratio, valve timing, and the like) of the engine 10 optimum to the combustion of the liquid fuel to be supplied from the fuel tank 2 to the engine 10 according to the specified properties. Then the engine control ECU 8 outputs a control signal indicating the optimum operational conditions to the engine 10 of the vehicle. Therefore, when the liquid fuel of the fuel tank 2 is supplied to the engine 10, the engine 10 is operated in its optimum operational conditions under control of the engine control ECU 8.

Accordingly, in the first embodiment, the fuel type identifying apparatus 1 can reliably identify the type of the liquid fuel of the fuel tank 2 by emitting a light beam of a predetermined emission spectrum to the liquid fuel, detecting a reflection spectrum of a light beam reflected on the liquid fuel, collating the detected reflection spectrum with the referential reflection spectrum corresponding to each fuel type, and finding out a particular type corresponding to the substantially same reflection spectrum as the detected reflection spectrum. Therefore, even through any of the fuel types allowed in the fuel tank 2 is currently held in the fuel tank 2, the engine 10 can be reliably operated under the operational conditions optimum to the combustion of the liquid fuel currently held in the fuel tank 2.

In this embodiment, the type of the liquid fuel of the fuel tank 2 is identified on the basis of the reflection spectrum. However, this embodiment should not be construed as limiting to the identification based on the reflection spectrum, and the identification may be based on spectral characteristics. More particularly, the control circuit 6 may calculate spectral characteristics of the liquid fuel of the fuel tank 2 from an emission spectrum and a reflection spectrum, collate the calculated spectral characteristics with referential spectral characteristics of each fuel type stored in the ROM 7, and find out a particular fuel type corresponding to referential spectral characteristics which are the substantially same as the calculated spectral characteristics.

Further, when the identification of the type of the liquid fuel based on the reflection spectrum is difficult because of a change of temperature or pressure (representing degree of environmental condition) of the liquid fuel, a temperature detector 3 or pressure detector may be disposed on a bottom of the fuel tank 2 to identify the type of the liquid fuel according to the detected reflection spectrum while considering a temperature or pressure detected by the temperature or pressure detector.

Further more, in this embodiment, the light sensor 4 is disposed inside of the fuel tank 2. However, the light sensor 4 may disposed outside of the fuel tank 2. In this case, a light beam is transmitted from the light sensor 4 to the liquid fuel of the fuel tank 2 through a window of the fuel tank 2. This window is made of a material (for example, glass) transparent to the light beam.

Figure 1B:
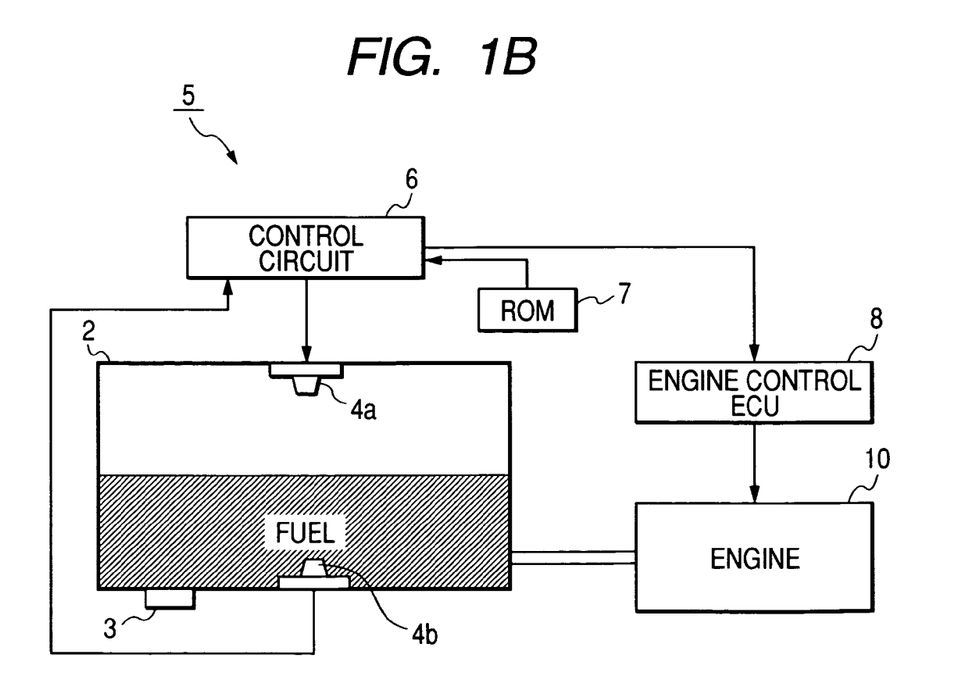
FIG. 1B is a view explanatorily and schematically showing a fuel type identifying apparatus according to a modification of the first embodiment of the present invention.

Next, a modification of the first embodiment is described with reference to FIG. 1B. FIG. 1B is a view explanatorily and schematically showing a fuel type identifying apparatus according to a modification of the first embodiment of the present invention.

In this modification, the light receiving element 4b is disposed on an inner bottom surface of the fuel tank 2 so as to face the light emitting element 4a through the liquid fuel.

In operation of a fuel type identifying apparatus 5, a portion of the light beam emitted from the light emitting element 4a is transmitted through the liquid fuel while being absorbed by the liquid fuel, and the other portion of the emitted light beam is reflected on the upper surface of the liquid fuel. The transmitted light beam is received by the light receiving element 4b, and the light receiving element 4b detects an absorption spectrum of the transmitted light beam and outputs a detection signal indicating the absorption spectrum to the control circuit 6.

The predetermined emission spectrum of the emitted light beam is changed to the absorption spectrum of the light beam transmitted through the liquid fuel according to the spectral characteristics of the liquid fuel, and spectral characteristics of each type of liquid fuel differ from those of the other fuel types. Therefore, the absorption spectrum of the light beam is peculiar to the type of the liquid fuel.

Accordingly, in the modification of the first embodiment, the fuel type identifying apparatus 5 can reliably identify the type of the liquid fuel of the fuel tank 2.

Embodiment 2

The inventor has noticed that values of electrical resistivity of various types of liquid fuels differ from one another at an arbitrary temperature in a predetermined range of temperature, and a value of electric resistance of the liquid fuel of each type depends on the electrical resistivity of the liquid fuel. The electrical resistivity represents a physical property, and a value of electric resistance represents a physical quantity.

Figure 2:
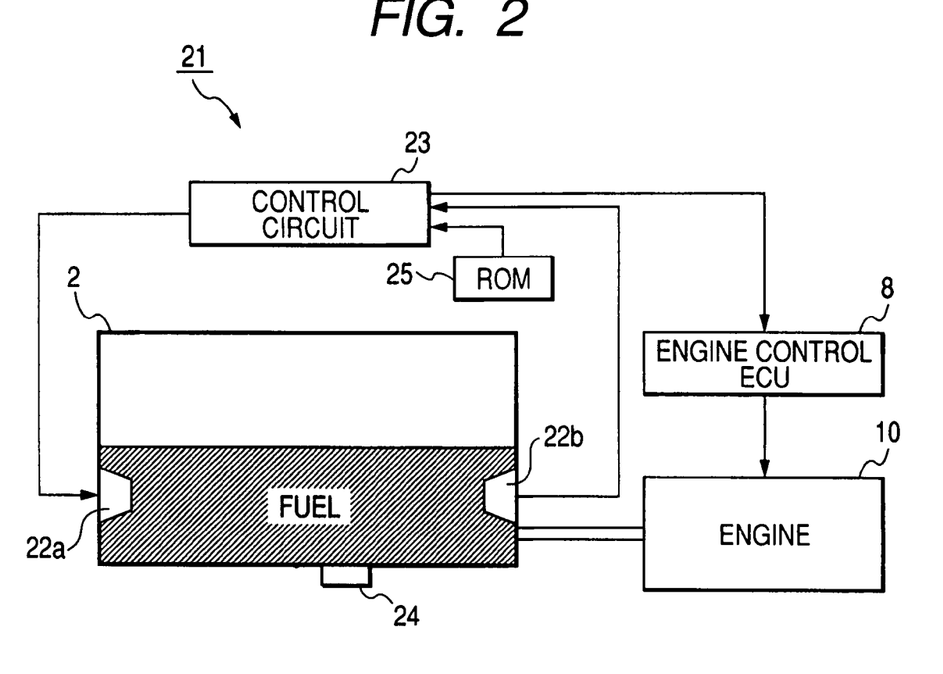
FIG. 2 is a view explanatorily and schematically showing a fuel type identifying apparatus according to a second embodiment of the present invention.

FIG. 2 is a view explanatorily and schematically showing a fuel type identifying apparatus according to a second embodiment.

As shown in FIG. 2, a fuel type identifying apparatus 21 mounted on a vehicle has two electrodes 22a and 22b representing a quantity detector, a temperature detector 24 attached to a bottom outer surface of the fuel tank 2, a control circuit 23 representing an identifying unit, and an ROM 25 representing a data storage.

The electrodes 22a and 22b are, respectively, attached on side surfaces of the fuel tank 2 opposite to each other near the bottom surface of the fuel tank 2, and a repositioned to face each other at a predetermined distance. The electrodes 22a and 22b detect an electric resistance of the liquid fuel placed between the electrodes 22a and 22b. Because the electrodes 22a and 22b are arranged near the bottom surface of the fuel tank 2, the electrodes 22a and 22b can detect an electric resistance of a low volume of liquid fuel. The temperature detector 24 representing a condition detector detects a temperature of the liquid fuel of the fuel tank 2. This temperature represents a degree of an environmental condition.

The ROM 25 stores data of a referential electric resistance at a referential temperature and a referential temperature dependency of the electric resistance for each of the liquid fuels of the types allowed in the fuel tank 2. The referential electric resistance and the referential temperature dependency of the electric resistance corresponding to each type of liquid fuel are obtained in advance by arranging the electrodes 22a and 22b placed at the predetermined distance from each other in a tank filled with the liquid fuel, measuring electric resistances of the liquid fuel at a large number of temperatures with the electrodes 22a and 22b, calculating a referential temperature dependency of the electric resistance from the measured electric resistances, and storing data of the measured electric resistance at the referential temperature and the calculated referential temperature dependency in the ROM 25 as the referential electric resistance and the referential temperature dependency of the electric resistance.

The control circuit 23 identifies the fuel type according to a temperature detected by the temperature detector 24, an electric resistance of the liquid fuel detected by the electrodes 22a and 22b and the data stored in the ROM 25.

In operation of the fuel type identifying apparatus 21, the control circuit 23 transmits a driving signal to the pair of electrodes 22a and 22b and the temperature detector 24. In response to the driving signal, the pair of electrodes 22a and 22b detects an electric resistance of the liquid fuel placed between the electrodes 22a and 22b and outputs a detection signal indicating the detected electric resistance to the control circuit 23. Further, the temperature detector 24 detects a temperature of the liquid fuel and outputs the detected temperature to the control circuit 23.

The control circuit 23 receiving the detected temperature calculates an electric resistance at the detected temperature from both the referential electric resistance and the referential temperature dependency of the electric resistance retrieved from the ROM 25 for each fuel type. Thereafter, the control circuit 23 receiving the detected electric resistance collates the detected electric resistance with the calculated electric resistance for each fuel type. Thereafter, the control circuit 23 finds out a particular type of the liquid fuel of the calculated electric resistance, which is the substantially same as the detected electric resistance, from the liquid fuel types. Then, the control circuit 23 distinguishes the type of the liquid fuel of the fuel tank 2 as the particular fuel type.

Accordingly, in the second embodiment, the fuel type identifying apparatus 21 can reliably identify the type of the liquid fuel of the fuel tank 2 by detecting an electric resistance of the liquid fuel at a detected temperature, calculating an electric resistance at the detected temperature from a referential electric resistance and a referential temperature dependency of the electric resistance for each fuel type, and collating the detected electric resistance with the calculated electric resistance of each fuel type. Therefore, in the same manner as in the first embodiment, the engine 10 is operated in its optimum operational conditions under control of the engine control ECU 8.

In this embodiment, the type of the liquid fuel of the fuel tank 2 is identified on the basis of the electric resistance. However, this embodiment should not be construed as limiting to the identification based on the electric resistance, and the identification may be based on electrical resistivity. More particularly, the control circuit 23 may calculate a value of electrical resistivity of the liquid fuel of the fuel tank 2 from the detected electric resistance, the predetermined distance between the electrodes 22a and 22b and shapes of the electrodes 22a and 22b, collate the calculated electrical resistivity with a referential electrical resistivity of each fuel type stored in the ROM 25, and find out a particular fuel type of the referential electrical resistivity which is the substantially same as the calculated electrical resistivity.

Embodiment 3

The inventor has noticed that the composition of components of a vapor vaporized from each of various types of liquid fuels differs from those of the other types of liquid fuels at an arbitrary temperature in a predetermined range of temperature, and a smell of a liquid fuel relating to a degree of change in electric resistance of a smell sensor depends on the components of a vapor vaporized from the liquid fuel. The composition of components represents a chemical property, and a smell of a liquid fuel represents a chemical quantity of the liquid fuel depending on the chemical property.

Figure 3:
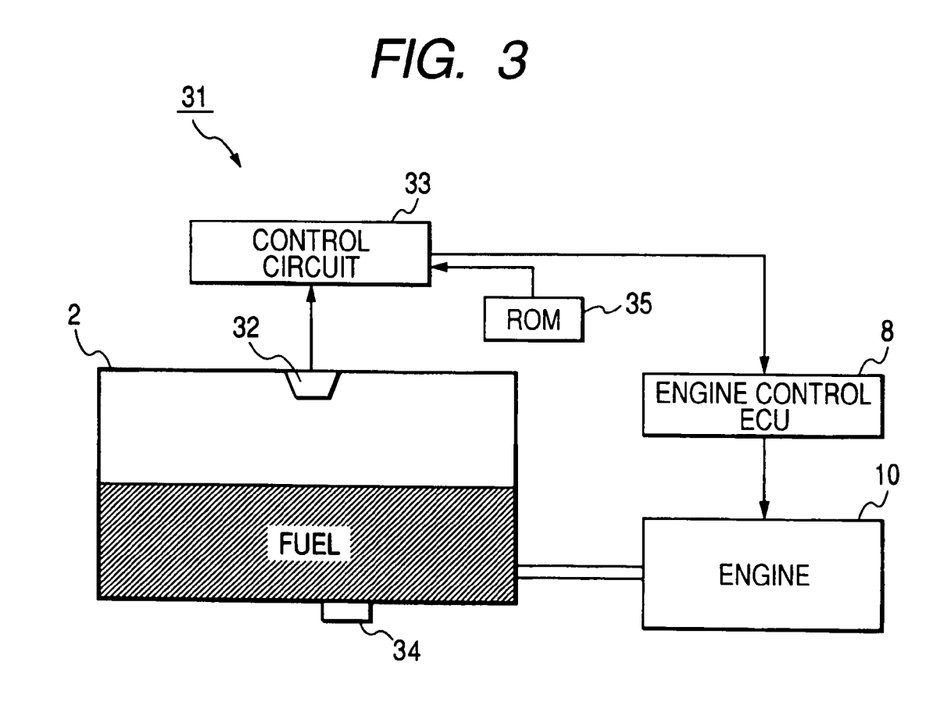
FIG. 3 is a view explanatorily and schematically showing a fuel type identifying apparatus according to a third embodiment of the present invention.

FIG. 3 is a view explanatorily and schematically showing a fuel type identifying apparatus according to a third embodiment.

As shown in FIG. 3, a fuel type identifying apparatus 31 mounted on a vehicle has a smell sensor 32 attached on an inner upper surface (or a lid) of the fuel tank 2, a temperature detector 34 attached to a bottom outer surface of the fuel tank 2, a control circuit 33 representing an identifying unit, and an ROM 35 representing a data storage.

The smell sensor 32 representing a quantity detector is placed in a vapor vaporized from the liquid fuel and detects a smell of the vapor as a smell of the liquid fuel. The smell sensor 32 is made of a crystal oscillator coated with a bimolecular sensitive film. In the crystal oscillator, an electric resistance of the sensitive film is changed in response to components of a vapor vaporized from the liquid fuel. Therefore, the smell sensor 32 detects a degree of change in its electric resistance as a detected smell.

The ROM 35 stores data of a plurality of referential smells corresponding to a plurality of temperatures for each fuel type allowed in the fuel tank 2. The referential smells corresponding to each type of liquid fuel are obtained in advance by putting the liquid fuel in a tank with the smell sensor 32, measuring degrees of change in the electric resistance of the smell sensor 32 while changing the temperature of the fuel liquid, and storing the measured degrees of change in the ROM 35 as data of the referential smells.

The control circuit 33 identifies the fuel type according to a smell detected by the smell sensor 32, a temperature detected by the temperature detector 34 and the data of the ROM 35.

In operation of the fuel type identifying apparatus 31, the control circuit 33 transmits a driving signal to the smell sensor 32 and the temperature detector 34. In response to the driving signal, the smell sensor 32 receives a vapor vaporized from the liquid fuel of the fuel tank 2 and detects a degree of change in its electric resistance as a smell. Then, the smell sensor 32 outputs a detection signal indicating a smell corresponding to the degree of change in the electric resistance. The temperature detector 34 detects a temperature of the fuel liquid. The composition of the vapor changes with the temperature of the fuel liquid, so that the smell detected in the smell sensor 32 changes with the temperature of the fuel liquid.

The control circuit 33 receiving the temperature detected by the temperature detector 34 and the smell detected by the smell sensor 32 retrieves the referential smells related to the detected temperature for the fuel types from the ROM 35. Then, the control circuit 33 collates the detected smell with the referential smell corresponding to the detected temperature for each fuel type, and finds out a particular fuel type, which corresponds to the substantially same smell as the detected smell, from the types of the liquid fuels. Therefore, the control circuit 23 distinguishes the liquid fuel of the fuel tank 2 as the particular fuel type.

Accordingly, in the third embodiment, the fuel type identifying apparatus 31 can reliably identify the type of the liquid fuel of the fuel tank 2 by detecting a smell in the smell sensor 32 at a detected temperature, and collating the detected smell with the referential smell of each fuel type at the detected temperature. Therefore, in the same manner as in the first embodiment, the engine 10 is operated in its optimum operational conditions under control of the engine control ECU 8.

In this embodiment, the smell sensor 32 is made of a crystal oscillator coated with one type of bimolecular sensitive film sensitive to one type of smell. However, the smell sensor 32 may be made of a crystal oscillator coated with a plurality of types of bimolecular sensitive films sensitive to a plurality of types of smells (for example, a smell peculiar to aromatic compound, a smell peculiar to paraffin hydrocarbon, a smell peculiar to olefin hydrocarbon, a smell peculiar to vegetable oil, a smell peculiar to sulfur, and the like). In this case, a change of an electric resistance of each type of sensitive film is measured as a strength of the corresponding smell type. Therefore, a plurality of strengths of the smell types can be detected. Accordingly, the type of the fuel liquid of the fuel tank 2 can further precisely be identified.

Embodiment 4

The inventor has noticed that values of saturation vapor pressure of various types of liquid fuels differ from one another at an arbitrary temperature in a predetermined range of temperature. The saturation vapor pressure represents a physical property, and a value of the saturation vapor pressure represents a physical quantity.

Figure 4:
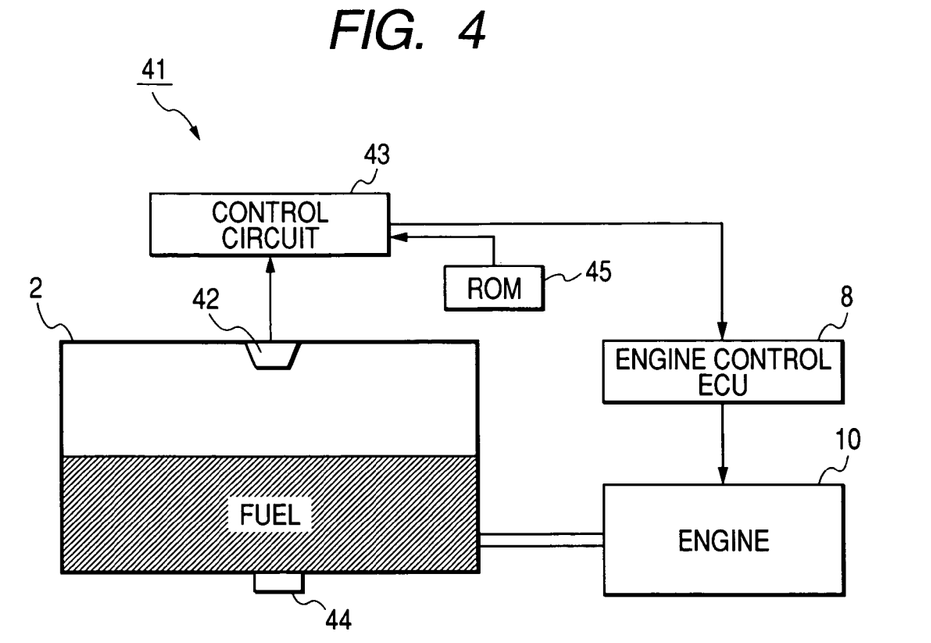
FIG. 4 is a view explanatorily and schematically showing a fuel type identifying apparatus according to a fourth embodiment of the present invention.

FIG. 4 is a view explanatorily and schematically showing a fuel type identifying apparatus according to a fourth embodiment.

As shown in FIG. 4, a fuel type identifying apparatus 41 mounted on a vehicle has a vapor pressure sensor 42 attached on an inner upper surface (or a lid) of the fuel tank 2, a temperature detector 44 attached to a bottom outer surface of the fuel tank 2, a control circuit 43 representing an identifying unit, and an ROM 45 representing a data storage.

The vapor pressure sensor 42 representing a quantity detector detects a vapor pressure of the liquid fuel saturated in the fuel tank 2. The vapor pressure sensor 42 is made of a pressure sensor, for example, of a semiconductor diaphragm type, an electrostatic capacitor type, an elastic diaphragm type, a piezo type, a vibration type, a bourdon tube type, a bellows type or the like. The temperature detector 44 detects a temperature of the liquid fuel of the fuel tank 2.

The ROM 45 stores data of a referential saturation vapor pressure at a referential temperature and a referential temperature dependency of the saturation vapor pressure for each fuel type allowed in the fuel tank 2. The referential saturation vapor pressure and the referential temperature dependency of the saturation vapor pressure corresponding to each type of liquid fuel are obtained by filling a tank with the liquid fuel, measuring vapor pressures of the liquid fuel saturated in the tank while changing the temperature of the liquid fuel, calculating a referential temperature dependency of the saturation vapor pressure from the measured vapor pressures, and storing data of the saturation vapor pressure measured at the referential temperature and the calculated referential temperature dependency in the ROM 45 as the referential saturation vapor pressure and the referential temperature dependency of the saturation vapor pressure.

The control circuit 43 identifies the fuel type according to a vapor pressure of the liquid fuel detected by the vapor pressure sensor 42, a temperature detected by the temperature detector 44 and the data of the ROM 45.

In operation of the fuel type identifying apparatus 41, the control circuit 43 transmits a driving signal to the vapor pressure sensor 42 and the temperature detector 44. In response to the driving signal, the vapor pressure sensor 42 detects a vapor pressure of the liquid fuel saturated in the fuel tank 2 and outputs a detection signal indicating the detected vapor pressure to the control circuit 43. The temperature detector 44 detects a temperature of the liquid fuel and outputs the detected temperature to the control circuit 43.

The control circuit 43 receiving the detected temperature calculates a referential saturation vapor pressure at the detected temperature from both the referential saturation vapor pressure and the referential temperature dependency of the saturation vapor pressure retrieved from the ROM 45 for each fuel type. Thereafter, the control circuit 43 receiving the detected vapor pressure from the vapor pressure sensor 42 collates the detected vapor pressure with the referential saturation vapor pressure at the detected temperature for each fuel type. Thereafter, the control circuit 43 finds out a particular type of the liquid fuel corresponding to the referential saturation vapor pressure, which is the substantially same as the detected vapor pressure, from the fuel types. Then, the control circuit 43 distinguishes the liquid fuel of the fuel tank 2 as the particular fuel type.

Accordingly, in the fourth embodiment, the fuel type identifying apparatus 41 can reliably identify the type of the liquid fuel of the fuel tank 2 by detecting a vapor pressure of the liquid fuel saturated in the fuel tank 2 at a detected temperature, calculating a saturation vapor pressure at the detected temperature from a referential saturation vapor pressure and a referential temperature dependency of the saturation vapor pressure for each fuel type, and collating the detected vapor pressure with the calculated saturation vapor pressure of each fuel type. Therefore, the engine 10 can be operated under its operational conditions optimum to the combustion of any of the fuel types supplied from the fuel tank 2.

Embodiment 5

The inventor has noticed that a level of sound spectral characteristics of each of various types of liquid fuels for ultrasonic waves differs from those of the other types of liquid fuels at an arbitrary temperature in a predetermined range of temperature, and a sound reflection spectrum of a sound depends on the sound spectral characteristics of the liquid fuel when a sound emission spectrum of the sound is fixed. The sound spectral characteristics represent a physical property, and the sound absorption spectrum represents a physical quantity.

Figure 5:
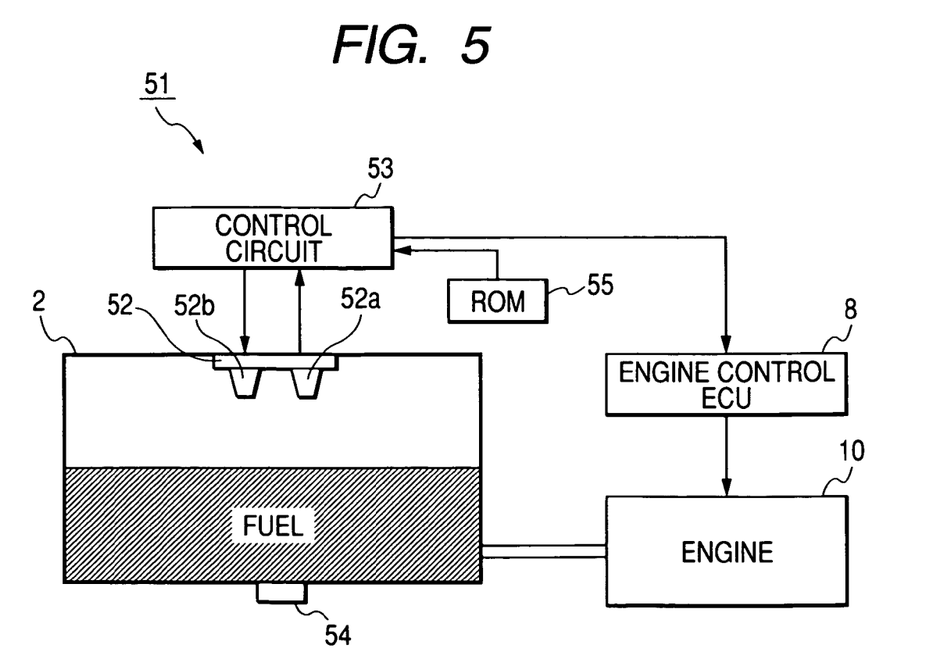
FIG. 5 is a view explanatorily and schematically showing a fuel type identifying apparatus according to fifth and sixth embodiments of the present invention.

FIG. 5 is a view explanatorily and schematically showing a fuel type identifying apparatus according to a fifth embodiment.

As shown in FIG. 5, a fuel type identifying apparatus 51 mounted on a vehicle has a sound sensor 52 attached on an inner upper surface (or a lid) of the fuel tank 2, a temperature detector 54 attached to a bottom outer surface of the fuel tank 2, a control circuit 53 representing an identifying unit, and an ROM 55 representing a data storage.

The sound sensor 52 representing a quantity detector has a speaker 52a outputting ultrasonic waves to the liquid fuel of the fuel tank 2 and a microphone 52b receiving ultrasonic waves reflected on the upper surface of the liquid fuel. The speaker 52a emits ultrasonic waves of a sound emission spectrum denoting an investigating signal to the liquid fuel of the fuel tank 2. The sound emission spectrum of the emitted ultrasonic waves is changed in dependence on sound spectral characteristics of the fuel type. The microphone 52b receives ultrasonic waves of a sound absorption spectrum. The set of speaker 52a and microphone 52b is made of a set of a piezo type speaker and a piezo type microphone, a set of condenser type speaker and condenser type microphone or the like. A piezoelectric semiconductor made of PZT (titanate lead zirconate) or the like is used for the piezo type speaker and microphone. When the speaker 52a and the microphone 52b are integrally formed with each other, the sound sensor 52 can be miniaturized, and restriction of an attaching position of the sound sensor 52 in the fuel tank 2 can be reduced. The temperature detector 54 detects a temperature of the liquid fuel of the fuel tank 2.

The ROM 55 stores data of a plurality of referential sound absorption spectra corresponding to a plurality of temperatures for each fuel type allowed in the fuel tank 2. The referential sound absorption spectra corresponding to each type of liquid fuel are obtained in advance by putting the liquid fuel in a tank having the same shape as that of the fuel tank 2, emitting ultrasonic waves of the sound emission spectrum to the liquid fuel while changing the temperature of the liquid fuel, receiving ultrasonic waves reflected on the surface of the liquid fuel for each temperature, measuring a sound reflection spectrum of the reflected ultrasonic waves for each temperature, and storing data of the measured sound reflection spectra in the ROM 55 as the referential sound reflection spectra.

The control circuit 53 identifies the fuel type according to a sound reflection spectrum detected by the sound sensor 52, a temperature detected by the temperature detector 54 and the data of the ROM 55.

In operation of the fuel type identifying apparatus 51, the control circuit 53 transmits a driving signal to the sound sensor 52 and the temperature detector 54. In response to the driving signal, the speaker 52a outputs an investigation signal indicating ultrasonic waves of a predetermined sound emission spectrum toward the liquid fuel of the fuel tank 2, and the temperature detector 54 outputs a detected temperature of the liquid fuel to the control circuit 53. A portion of the emitted ultrasonic waves are absorbed by the liquid fuel, and the other portion of the emitted ultrasonic waves are reflected on the upper surface of the liquid fuel as reflected ultrasonic waves of a sound reflection spectrum. The reflected ultrasonic waves are received in the microphone 52b, and the microphone 52b outputs a detection signal indicating the reflected ultrasonic waves to the control circuit 53.

A predetermined sound emission spectrum of ultrasonic waves is changed to a sound reflection spectrum of ultrasonic waves reflected on a liquid fuel according to sound spectral characteristics of the liquid fuel, and sound spectral characteristics of each type of liquid fuel differ from those of the other fuel types. Therefore, the sound reflection spectrum of ultrasonic waves reflected on a liquid fuel is peculiar to the type of the liquid fuel.

The control circuit 53 receiving the detected temperature and the detection signal retrieves a referential sound reflection spectrum of the detected temperature from the ROM 55 for each fuel type, and collates the detected sound reflection spectrum with the referential sound reflection spectrum for each fuel type. Thereafter, the control circuit 53 finds out a particular fuel type corresponding to the referential sound reflection spectrum, which is the substantially same an the detected sound reflection spectrum, from the fuel types. Therefore, the control circuit 53 distinguishes the liquid fuel of the fuel tank 2 as the particular fuel type.

Accordingly, in the fifth embodiment, the fuel type identifying apparatus 51 can reliably identify the type of the liquid fuel of the fuel tank 2 by detecting a sound reflection spectrum of ultrasonic waves reflected on the liquid fuel of the fuel tank 2, detecting a temperature of the liquid fuel, and collating the detected sound reflection spectrum with the referential sound reflection spectrum of the detected temperature corresponding to each fuel type. Therefore, the engine 10 can be operated in its operational conditions optimum to the combustion of any of the fuel types supplied from the fuel tank 2.

In this embodiment, the type of the liquid fuel of the fuel tank 2 is identified on the basis of the sound reflection spectrum. However, the identification may be based on sound spectral characteristics. More particularly, the control circuit 53 may calculate sound spectral characteristics of the liquid fuel of the fuel tank 2 from a sound emission spectrum and a sound reflection spectrum, collate the calculated sound spectral characteristics with referential sound spectral characteristics of each fuel type stored in the ROM 55, and find out a particular fuel type corresponding to referential sound spectral characteristics which are the substantially same as the calculated spectral characteristics.

Embodiment 6

The inventor has noticed that values of viscosity of various types of liquid fuels differ from one another at an arbitrary temperature in a predetermined range of temperature, and a sound speed of surface acoustic waves reflected in each type of liquid fuel depends on the value of viscosity of the type of liquid fuel when a predetermined sound speed of surface acoustic waves emitted to the liquid fuel is fixed. The viscosity represents a physical property, and a sound speed of the reflected surface acoustic waves represents a physical quantity depending on the degree of the physical property.

The fuel type identifying apparatus 51 shown in FIG. 5 is also used for an identifying apparatus according to the sixth embodiment.

The speaker 52a outputs surface acoustic waves at a predetermined sound speed as an investigation signal. The surface acoustic waves are reflected in the liquid fuel of the fuel tank 2. The microphone 52b receives reflected surface acoustic waves and outputs a detection signal indicating the reflected surface acoustic waves to the control circuit 53. In this case, a response sound speed of the reflected surface acoustic waves differs from the predetermined sound speed, and the response sound speed (or a difference between the predetermined sound speed and the response sound speed) depends on a value of viscosity of the liquid fuel. The value of viscosity of the liquid fuel depends on a temperature of the liquid fuel. Therefore, the control circuit 53 identifies a type of the liquid fuel of the fuel tank 2 according to the response sound speed, the data of the ROM 55 and a temperature detected in the temperature detector 54.

Accordingly, in the sixth embodiment, the fuel type identifying apparatus 51 can reliably identify the type of the liquid fuel of the fuel tank 2 by detecting a response sound speed of reflected surface acoustic waves. Therefore, the engine 10 can be operated in its operational conditions optimum to the combustion of any of the fuel types supplied from the fuel tank 2.

In this embodiment, the temperature detector 54 is disposed in the fuel tank 2. However, when the fuel type can be identified regardless of a change of temperature in the liquid fuel, no temperature detector is required in the identifying apparatus 51.

Embodiment 7

A fuel type identifying apparatus according to the seventh embodiment is configured by combining two or more selected from the identifying apparatuses 1, 21, 31, 41 and 51 according to the first to sixth embodiments. In this identifying apparatus, the type of the liquid fuel can be further reliably identified.

In each of the second, third, fifth and sixth embodiments, the temperature detector is disposed in the fuel tank 2. However, when a change of temperature in the liquid fuel does not influence on the identification of the fuel type based on the chemical or physical property (electric resistance, smell, sound reflection spectrum, or response sound speed), no temperature detector is required in the identifying apparatus.

Further, in each of the second, third, fourth, fifth and sixth embodiments, to prevent that at least two of chemical or physical properties of types of liquid fuels become the same value as each other, the identification of the fuel type is performed within the predetermined temperature range. However, when there is no probability that at least two of chemical or physical properties of types of liquid fuels become the same value as each other, the identification of the fuel type may be performed without limitation of the temperature.

Further, in each of the second, third, fourth, fifth and sixth embodiments, a temperature of the liquid fuel is detected as a degree of an environmental condition. However, the present invention is not limited to the temperature, and a pressure applied to the liquid fuel may be detected.

Further, in each of the embodiments, the control circuit finds out the particular type of the liquid fuel corresponding to the referential chemical or physical quantity which is the substantially same as the detected chemical or physical quantity. However, the control circuit may find out a particular type of the liquid fuel corresponding to one referential chemical or physical quantity most similar to the detected chemical or physical quantity.

Furthermore, in the first, fifth and sixth embodiment, the control circuit may initially find out a plurality of particular types of the liquid fuels each of which corresponds to the referential chemical or physical quantity similar to the detected chemical or physical quantity. In this case, the control circuit outputs an adjusting signal to the signal transmitter according to the particular types, and the signal transmitter adjusts the investigation signal to a modified investigation signal (for example, a laser beam having a modified range of wavelength and/or modified strength) appropriate to the detection of the chemical or physical quantity from each particular type of the liquid fuel and emits the modified investigation signal to the liquid fuel of the fuel tank 2. The control circuit finds out one particular type corresponding to the referential reflection spectrum most similar to the chemical or physical property received by the signal receiver. Accordingly, the fuel type identifying apparatus can further reliably identify the type of the liquid fuel.

Moreover, in the embodiments, the fuel tank 2 currently holds one of the fuel types. However, the fuel tank 2 may hold a blended liquid fuel as a type of liquid fuel. The blended liquid is obtained by blending one type of liquid fuel with another type or other types.

What is claimed is:

1. A fuel type identifying apparatus comprising:
   a quantity detector, which detects a plurality of physical or chemical quantities, from a liquid fuel, depending on a physical or chemical property of the liquid fuel, and outputs a detection signal indicating the physical or chemical quantities; and
   an identifying unit, which receives the detection signal from the quantity detector and identifies a type of the liquid fuel according to the physical or chemical quantities of the detection signal; and
   a data storage that stores a plurality of referential physical or chemical quantifies for each of a plurality of types of referential liquid fuels, the referential physical or chemical quantities for the referential liquid fuel of each of the types being obtained by outputting a first signal indicating a plurality of predetermined quantities to the referential liquid fuel to obtain a second signal from the referential liquid fuel, measuring a plurality of physical or chemical quantities of the second signal, and setting the measured physical or chemical quantities as the referential physical or chemical quantities, wherein the quantity detector comprises:

a signal transmitter, which produces an investigation signal indicating plurality of predetermined quantities that are changeable in response to the physical or chemical properties of the liquid fuel and outputs the investigation signal to the liquid fuel to induce the liquid fuel to change the predetermined quantities to the physical or chemical quantities; and a signal receiver that receives the physical or chemical quantities as the detection signal from the liquid fuel, wherein the identifying unit collates the physical or chemical quantities of the detection signal with the physical or chemical referential quantities of each type of referential liquid fuel stored in the data storage to obtain a plurality of collation results and identifies the type of the liquid fuel according to the collation results.

2. The fuel type identifying apparatus according to claim 1, wherein the data storage is adapted to store a plurality of spectral characteristics of a referential reflection spectrum as the referential physical quantities for each referential liquid fuel, the spectral characteristics of the referential reflection spectrum for each referential liquid fuel being obtained by outputting a first light beam having a predetermined spectrum to the referential liquid fuel to obtain a second light beam having a reflection spectrum from the referential liquid fuel, measuring the reflection spectrum of the second light beam and setting spectral characteristics of the measured reflection spectrum as the spectral characteristics of the referential reflection spectrum, the signal transmitter includes a light emitting element, which emits a light beam of a predetermined emission spectrum to the liquid fuel to induce the liquid fuel to change the emitted light beam to a reflected light beam having a reflection spectrum, the signal receiver includes a light receiving element, which receives the reflected light beam from the liquid fuel, and the identifying unit receives the reflected light beam from the light receiving element, collates a plurality of spectral characteristics of the reflection spectrum of the reflected light beam with the spectral characteristics of referential reflection spectrum of each referential liquid fuel stored in the data storage to obtain a plurality of collation results, and identifies the liquid fuel according to the collation results.

3. The fuel type identifying apparatus according to claim 1, wherein the data storage is adapted to store plurality of spectral characteristics of a referential absorption spectrum as a plurality of referential physical quantities for each referential liquid fuel, the spectral characteristics of the referential absorption spectrum for each referential liquid fuel being obtained by outputting a first light beam having a predetermined emission spectrum to the referential liquid fuel to obtain a second light beam having an absorption spectrum from the referential liquid fuel, measuring a plurality of spectral characteristics of the absorption spectrum of the second light beam and setting the spectral characteristics of the measured absorption spectrum as the spectral characteristics of the referential absorption spectrum, the signal transmitter includes a light emitting element that emits a light beam of the predetermined emission spectrum to the liquid fuel to induce the liquid fuel to change the emitted light beam to a transmitted light beam having an absorption spectrum, the signal receiver includes a light receiving element, which receives the transmitted light beam from the liquid fuel, and the identifying unit receives the transmitted light beam from the light receiving element, collates a plurality of spectral characteristics of the absorption spectrum of the transmitted light beam with the spectral characteristics of each referential absorption spectrum stored in the data storage to obtain a plurality of collation results and identifies the liquid fuel according to the collation results.

4. The fuel type identifying apparatus according to claim 1, wherein the data storage is adapted to store a plurality of ultrasonic waves of a referential sound spectrum having plurality of ultrasonic waves as referential, physical quantities for each referential liquid fuel, the ultrasonic waves of the referential sound spectrum for each referential liquid fuel being obtained by outputting a predetermined sound emission spectrum to the referential liquid fuel to obtain ultrasonic waves of a sound reflection spectrum from the referential liquid fuel, measuring a plurality of ultrasonic waves of the sound reflection spectrum and setting the ultrasonic waves of the measured sound reflection spectrum as the ultrasonic waves of the referential sound spectrum, the signal transmitter includes a speaker, which outputs ultrasonic waves of the predetermined sound emission spectrum to the liquid fuel to induce the liquid fuel to change the outputted ultrasonic waves of the predetermined sound emission spectrum to reflected ultrasonic waves of a sound reflection spectrum, the signal receiver includes a microphone, which receives the reflected ultrasonic waves of the sound reflection spectrum from the liquid fuel, and the identifying unit receives the reflected ultrasonic waves of the sound reflection spectrum from the microphone, collates the reflected ultrasonic waves of the sound reflection spectrum with the ultrasonic waves of each referential sound spectrum stored in the data storage to obtain a plurality of collation results and identifies the liquid fuel according to the collation results.

5. The fuel type identifying apparatus according to claim 1, wherein the data storage is adapted to store a plurality of surface acoustic waves of a referential sound speed as a plurality of referential physical quantities for each referential liquid fuel, the surface acoustic waves of the referential sound speed for each referential liquid fuel being obtained by outputting a predetermined sound speed to the referential liquid fuel to obtain a sound speed from the referential liquid fuel, measuring surface acoustic waves of the obtained sound speed and setting the surface acoustic waves of the measured sound speed as the surface acoustic waves of the referential sound speed, the signal transmitter includes a speaker, which outputs surface acoustic waves of the predetermined sound speed to the liquid fuel to induce the liquid fuel to change the outputted surface acoustic waves of the predetermined sound speed to reflected surface acoustic waves of a changed sound speed, and the signal receiver includes a microphone, which receives the reflected surface acoustic waves of the changed sound speed from the liquid fuel, and the identifying unit receives the reflected surface acoustic waves of the changed sound speed from the microphone, collates the reflected surface acoustic waves of the changed sound speed with the surface acoustic waves of each referential sound speed stored in the data storage to obtain a plurality of collation results, and identifies the liquid fuel according to the collation results.

6. A fuel type identifying apparatus comprising:

a quantity detector, which detects a plurality of physical or chemical quantities, from a liquid fuel, depending on a physical or chemical property of the liquid fuel, and outputs a detection signal indicating the physical or chemical quantities;

an identifying unit, which receives the detection signal from the quantity detector and identifies a type of the liquid fuel according to the physical or chemical quantities of The detection signal; and a data storage, which stores a plurality of referential physical or chemical quantities for each of a plurality of types of referential liquid fuels, the referential physical or chemical quantities for the referential liquid fuel of each of the types being obtained by measuring a plurality of physical or chemical quantities of the referential liquid fuel depending on the physical or chemical property and setting the physical or chemical quantities as the referential physical or chemical quantities, wherein the identifying unit collates the physical or chemical quantities of the detection signal with the physical or chemical referential quantities of each type of referential liquid fuel stored in the data storage to obtain a plurality of collation results and identifies the type of the liquid fuel according to the collation results.

7. A fuel type identifying apparatus comprising:

a quantity detector, which detects a plurality of physical or chemical quantities from a liquid fuel and outputs a detection signal indicating the physical or chemical quantities; and an identifying unit, which receives the detection signal from the quantity detector and identifies a type of the liquid fuel according to the physical or chemical quantities of the detection signal a data storage, which stores a plurality of referential physical or chemical quantities for each of a plurality of types of referential liquid fuels, the referential physical or chemical quantities for each type of referential liquid fuel being obtained by outputting a first signal indicating a plurality of predetermined quantities to the referential liquid fuel to obtain a second signal from the referential liquid fuel, measuring a plurality of physical or chemical quantities of the second signal, and setting the measured physical or chemical quantities as the referential physical or chemical quantities, wherein the quantity detector comprises:

a signal transmitter, which produces an investigation signal indicating the predetermined quantities of the liquid fuel and outputs the investigation signal to the liquid fuel to induce the liquid fuel to change the predetermined quantities to the physical or chemical quantities; and a signal receiver, which receives the physical or chemical quantities as the detection signal from the liquid fuel, wherein the identifying unit collates the physical or chemical quantities of the detection signal with the physical or chemical referential quantities of each type of referential liquid fuel stored in the data storage to obtain a plurality of collation results and identifies the type of the liquid fuel according to the collation results.

8. The fuel type identifying apparatus according to claim 7, wherein the data storage is adapted to store plurality of spectral characteristics of a referential absorption spectrum as a plurality of referential physical quantities for each referential liquid fuel, the spectral characteristics of the referential absorption spectrum for each referential liquid fuel being obtained by outputting a first light beam having a predetermined emission spectrum to the referential liquid fuel to obtain a second light beam having an absorption spectrum from the referential liquid fuel, measuring a plurality of spectral characteristics of the absorption spectrum of the second light beam and setting the spectral characteristics of the measured absorption spectrum as the spectral characteristics of the referential absorption spectrum, the signal transmitter includes a light emitting element, which emits a light beam of the predetermined emission spectrum to the liquid fuel to induce the liquid fuel to change the emitted light beam to a transmitted light beam having an absorption spectrum, the signal receiver includes a light receiving element, which receives the transmitted light beam from the liquid fuel, and the identifying unit receives the transmitted light beam from the light receiving element, collates a plurality of spectral characteristics of the absorption spectrum of the transmitted light beam with the spectral characteristics of the referential absorption spectrum of each referential liquid fuel stored in the data storage to obtain a plurality of collation results, and identifies the liquid fuel according to the collation results.

9. The fuel type identifying apparatus according to claim 7, wherein the data storage is adapted to store a plurality of ultrasonic waves of a referential sound spectrum as a plurality of referential physical quantities for each referential liquid fuel, the ultrasonic waves of the referential sound spectrum for each referential liquid fuel being obtained by outputting a predetermined sound emission spectrum, to the referential liquid fuel to obtain a sound reflection spectrum from the referential liquid fuel measuring a plurality of ultrasonic waves of the sound reflection spectrum and setting the ultrasonic waves of the measured sound reflection spectrum as the ultrasonic waves of the referential sound spectrum, the signal transmitter includes a speaker, which outputs ultrasonic waves of the predetermined sound emission spectrum to the liquid fuel to induce the liquid fuel to change the outputted ultrasonic waves of the predetermined sound emission spectrum to reflected ultrasonic waves of a sound reflection spectrum, the signal receiver includes a microphone, which receives the reflected ultrasonic waves of the sound reflection spectrum from the liquid fuel, and the identifying unit receives the reflected ultrasonic waves of the sound reflection spectrum from the microphone, collates the reflected ultrasonic waves of the sound reflection spectrum with the ultrasonic waves of the referential sound spectrum of each referential liquid fuel stored in the data storage to obtain a plurality of collation results, and identifies the liquid fuel according to the collation results.

10. The fuel type identifying apparatus according to claim 7, wherein
the data storage is adapted to store a plurality of surface acoustic waves of a referential sound speed as a plurality of referential physical quantities for each referential liquid fuel, the surface acoustic waves of the referential sound speed for each referential liquid fuel being obtained by outputting a predetermined sound speed to the referential liquid fuel to obtain a sound speed from the referential liquid fuel, measuring a plurality of surface acoustic waves of the sound speed and setting the surface acoustic waves of the measured sound speed as the surface acoustic waves of the referential sound speed,
the signal transmitter includes a speaker, which outputs surface acoustic waves of the predetermined sound speed to the liquid fuel to induce the liquid fuel to change the outputted surface acoustic waves of the predetermined sound speed to reflected surface acoustic waves of a changed sound speed,
the signal receiver includes a microphone, which receives the reflected surface acoustic waves of the changed sound speed from the liquid fuel, and
the identifying unit receives the reflected surface acoustic waves of the changed sound speed from the microphone, collates the reflected surface acoustic waves of the changed sound speed with the surface acoustic waves of the referential sound speed of each referential liquid fuel stored in the data storage to obtain a plurality of collation results, and identifies the liquid fuel according to the collation results.

11. The fuel type identifying apparatus according to claim 7, wherein
the data storage is adapted to store a plurality of spectral characteristics of a referential reflection spectrum as a plurality of referential physical quantities for each referential liquid fuel, the spectral characteristics of the referential reflection spectrum for each referential liquid fuel being obtained by outputting a first light beam having a predetermined spectrum to the referential liquid fuel to obtain a second light beam having a reflection spectrum from the referential liquid fuel, measuring a plurality of spectral characteristics of the reflection spectrum of the second light beam and setting the spectral characteristics of the measured reflection spectrum as the spectral characteristics of the referential reflection spectrum,
the signal transmitter includes a light emitting element, which emits a light beam of the predetermined emission spectrum to the liquid fuel to induce the liquid fuel to change the emitted light beam to a reflected light beam having a reflection spectrum, and
the signal receiver includes a light receiving element, which receives the reflected light beam from the liquid fuel, and
the identifying unit receives the reflected light beam from the light receiving element, collates a plurality of spectral characteristics of the reflection spectrum of the reflected light beam with the spectral characteristics of the referential reflection spectrum of each referential liquid fuel stared in the data storage to obtain a plurality of collation results and identifies the liquid fuel according to the collation results.

12. A fuel type identifying apparatus comprising:
a quantity detector, which detects plurality of physical or chemical quantities from a liquid fuel and outputs a detection signal indicating the physical or chemical quantities;
an identifying unit, which receives the detection signal from the quantity detector and identifies a type of the liquid fuel according to the physical or chemical quantities of the detection signal; and
a data storage, which stores a plurality of referential physical or chemical quantities for each of a plurality of types of referential liquid fuels, the referential physical or chemical quantities for the referential liquid fuel of each of the types being obtained by measuring a plurality of physical or chemical quantities of the referential liquid fuel and setting the measured physical or chemical quantities as the referential physical or chemical quantities,
wherein the identifying unit collates the physical or chemical quantities of the detection signal with the physical or chemical referential quantities of each type of referential liquid fuel stored in the data storage to obtain a plurality of collation results and identifies the type of the liquid fuel according to the collation results.

* * * * *

UNITED STATES PATENT AND TRADEMARK OFFICE
CERTIFICATE OF CORRECTION

PATENT NO.         : 7,406,871 B2
APPLICATION NO.    : 11/032222
DATED              : August 5, 2008
INVENTOR(S)        : Sugiura Page 1 of 1

It is certified that error appears in the above-identified patent and that said Letters Patent is hereby corrected as shown below:

Title Page

Correct the Assignee's resident city (item 73) of the original Letters Patent to read as:

Item (73) Assignee:   DENSO CORPORATION, Kariya (JP)

Signed and Sealed this

Twenty-first Day of April, 2009

JOHN DOLL
*Acting Director of the United States Patent and Trademark Office*